United States Patent
Hwang et al.

(10) Patent No.: US 8,900,609 B2
(45) Date of Patent: Dec. 2, 2014

(54) SWEAT-ABSORBING COSMETIC PRODUCT AND METHOD FOR THE PRODUCTION THEREOF

(75) Inventors: Donna Hui-Ing Hwang, Leonia, NJ (US); Ralph Macchio, Sparta, NJ (US); Domnica Cernasov, Ringwood, NJ (US); Salvatore Barone, Staten Island, NY (US)

(73) Assignee: Coty B.V., Haarlem (NL)

( * ) Notice: Subject to any disclaimer, the term of this patent is extended or adjusted under 35 U.S.C. 154(b) by 1465 days.

(21) Appl. No.: 11/568,059
(22) PCT Filed: Apr. 22, 2005
(86) PCT No.: PCT/EP2005/004495
§ 371 (c)(1), (2), (4) Date: Oct. 18, 2006
(87) PCT Pub. No.: WO2005/102255
PCT Pub. Date: Nov. 3, 2005

(65) Prior Publication Data
US 2009/0220555 A1    Sep. 3, 2009

(30) Foreign Application Priority Data
Apr. 22, 2004 (DE) .......................... 10 2004 020 646

(51) Int. Cl.
| | |
|---|---|
| *A61K 8/02* | (2006.01) |
| *A61K 8/72* | (2006.01) |
| *A61Q 15/00* | (2006.01) |
| *A61K 8/25* | (2006.01) |
| *A61K 8/365* | (2006.01) |
| *A61K 8/73* | (2006.01) |

(52) U.S. Cl.
CPC . *A61K 8/25* (2013.01); *A61K 8/365* (2013.01); *A61K 8/73* (2013.01); *A61Q 15/00* (2013.01); *A61K 2800/412* (2013.01)
USPC .......................................... 424/401; 424/78.3

(58) Field of Classification Search
None
See application file for complete search history.

(56) References Cited

U.S. PATENT DOCUMENTS

| | | | |
|---|---|---|---|
| 4,264,586 A | | 4/1981 | Callingham et al. |
| 4,508,705 A | * | 4/1985 | Chaudhuri et al. ............. 424/47 |

(Continued)

FOREIGN PATENT DOCUMENTS

| | | |
|---|---|---|
| DE | 28 37 088 A1 | 3/1979 |
| DE | 102 06 237 A1 | 8/2003 |

(Continued)

OTHER PUBLICATIONS

Handbook of Cosmetics, Nikko Chemical Co., Ltd. p. 97, Nov. 1, 1969.

(Continued)

*Primary Examiner* — Scott Long
*Assistant Examiner* — Sarah Alawadi
(74) *Attorney, Agent, or Firm* — Norris McLaughlin & Marcus, P.A.

(57) ABSTRACT

The invention relates to a—in particular—hydrous, sweat-absorbing cosmetic product, e.g. a deodorant, containing a sweat-absorbing complex. The invention also relates to a method for the production of said complex and said cosmetic product.
The cosmetic product of the invention includes
i) a base formulation, and
ii) a sweat-absorbing complex comprising
   (a) at least one water-absorbing component,
   (b) at least one surface-active agent,
   (c) at least one electrolyte, and
   (d) at least one solvent and/or at least one vehicle.
The sweat-absorbing complex in the base formulation is present in the form of emulsified particles. The particles consist of a three-dimensional, water-swellable network of said at least one water-absorbing component and are at least partially covered with said at least one surface-active agent. Said at least one electrolyte is incorporated at least partially in the interstices of the three-dimensional network of said at least one water-absorbing component.

27 Claims, 4 Drawing Sheets

(56) References Cited

U.S. PATENT DOCUMENTS

| | | | |
|---|---|---|---|
| 4,650,670 A | | 3/1987 | Callingham et al. |
| 5,271,934 A | * | 12/1993 | Goldberg et al. ............. 424/401 |
| 5,500,209 A | | 3/1996 | Mendolia et al. |
| 6,025,007 A | | 2/2000 | Krawczyk |
| 6,126,951 A | * | 10/2000 | Fogel ............................ 424/401 |
| 6,187,300 B1 | | 2/2001 | Motley et al. |
| 6,372,280 B1 | * | 4/2002 | Gonsalves et al. ............ 426/564 |
| 6,426,062 B1 | * | 7/2002 | Chopra et al. .................. 424/65 |
| 6,573,687 B2 | | 6/2003 | Kimura et al. |
| 6,605,288 B1 | * | 8/2003 | Okawa et al. ................. 424/401 |
| 2001/0014342 A1 | | 8/2001 | De La Charriere et al. |
| 2001/0033150 A1 | | 10/2001 | Kimura et al. |
| 2001/0046507 A1 | * | 11/2001 | Dietz et al. .................... 424/401 |
| 2003/0053970 A1 | | 3/2003 | Bruening et al. |
| 2003/0065087 A1 | * | 4/2003 | Nambu et al. ................. 524/588 |
| 2003/0186826 A1 | * | 10/2003 | Eccard et al. ................. 510/130 |
| 2003/0208831 A1 | * | 11/2003 | Lazar et al. ........................ 2/69 |
| 2004/0001799 A1 | | 1/2004 | Lu et al. |
| 2004/0131645 A1 | * | 7/2004 | Williams et al. .............. 424/400 |
| 2005/0191325 A1 | * | 9/2005 | Remon .......................... 423/657 |
| 2008/0317694 A1 | | 12/2008 | Bruening et al. |

FOREIGN PATENT DOCUMENTS

| | | |
|---|---|---|
| DE | 102 08 550 A1 | 9/2003 |
| DE | 10052966 | 5/2005 |
| EP | 0 701 812 A | 3/1996 |
| EP | 1139481 A1 | 10/2001 |
| EP | 1 258 290 A | 11/2002 |
| EP | 1 338 266 A | 8/2003 |
| EP | 1 338 268 A1 | 8/2003 |
| JP | 50-126820 | 10/1975 |
| JP | 56-161408 A | 12/1981 |
| JP | 57-167302 A | 10/1982 |
| JP | 2002249421 | 9/2002 |
| JP | 2003-525877 | 9/2003 |
| WO | 03 026608 A | 4/2003 |
| WO | 03/030853 A1 | 4/2003 |
| WO | 03 105790 A | 12/2003 |

OTHER PUBLICATIONS

Final Rejection from related U.S. Appl. No. 11/568,016, mailed Mar. 20, 2012.

Courtney, Sr., Donald L.; "Surfactants in Cosmetics", Surfactant Science Series, 1997, pp. 127-130; vol. 68, Marcel Dekker, Inc., New York, New York, United States of America.

* cited by examiner

SWEAT-ABSORBING COSMETIC PRODUCT AND METHOD FOR THE PRODUCTION THEREOF

The invention relates to a—in particular—hydrous, sweat-absorbing cosmetic product, e.g. a deodorant, containing a base formulation and a sweat-absorbing complex. The invention also relates to a method for the production of said complex and said cosmetic product.

Cosmetic products with an anti-perspiration effect are well-known, and different classes of products can be distinguished. Deodorants eliminate unpleasant odors originating from bacterial decomposition of sweat. Deodorants therefore frequently include antibacterial substances as well as fragrant substances such as aromatic essences. Many ethereal oils have both antibacterial and fragrant properties, for which reason they are frequently used in deodorants. Products inhibiting sweat production per se, so-called antiperspirants, include adstringent agents as active substances (antiperspirant actives), especially aluminum or zirconium salts. Basically, deodorant products contain water, whereas traditional antiperspirants (including suspended adstringents in a non-polar phase such as silicone oil or mineral oil) are substantially free of water in order to prevent polymerization of the adstringent agents. Nevertheless, a new generation of transparent antiperspirants has recently been developed which has gained popularity owing to its aesthetic appearance. This new generation of antiperspirants are emulsions usually containing propylene glycol, adstringents, water and oils. However, this type of antiperspirants is less active than the traditional type due to polymerization of the adstringent agents.

Both classes of products—deodorants and antiperspirants—may additionally include substances capable of absorbing sweat, thereby imparting a fresh and dry feeling to the skin. Conventional sweat-absorbing components are, for example, polymers such as natural or chemically modified polysaccharides or polysaccharide gums, or synthetic polymers. Such polymers form three-dimensional networks capable of absorbing water. One common problem of hydrous products (comprising emulsion type deodorants and antiperspirants) is that the water-absorbing component, once incorporated in a hydrous formulation, rapidly loses its absorptive capacity.

From WO 03/030853, a substantially water-free forearm product is known which includes a special water-absorbing polymer, a volatile silicone and a gelling agent, and optionally small amounts of a surfactant (to stabilize the formulation), an antiperspirant active substance or deodorizing agent, a non-volatile silicone and an emulsifier. The product is a suspension wherein the water-absorbing polymer is present in the form of dispersed particles. This formulation is not suitable for use in standard hydrous deodorant formulations because the water-absorbing polymer undergoes swelling in water, losing its water storage capacity.

The object of the present invention is to provide a sweat-absorbing cosmetic product, especially a deodorant, which has increased and sustaining water absorption capacity, particularly in hydrous formulations, and overcomes the formulation problems of well-known deodorant products.

Said object is accomplished by means of a sweat-absorbing cosmetic product having the features as in claim 1. The product according to the invention includes (in parts by weight):
i) a base formulation, and
ii) a sweat-absorbing complex comprising
  (a) 0.1 to 90% of at least one water-absorbing component,
  (b) 0.1 to 80% of at least one surface-active agent,
  (c) 0.001 to 20%, particularly 0.01 to 20%, of at least one electrolyte, and
  (d) optionally 0 to 50% of at least one solvent and/or at least one vehicle.

A crucial feature is that the sweat-absorbing complex in the base formulation is present in the form of emulsified particles which consist of a three-dimensional, water-swellable polymer network of said at least one water-absorbing component, and which are at least partially covered (coated) with said at least one surface-active agent.

In the complex, said at least one water-absorbing component, which does not undergo complete swelling in the solvent and/or vehicle, but is capable of swelling in water (to form particles of a three-dimensional gel-like polymer network), is protected from absorption of water from a base formulation of the cosmetic product owing to a coating (cover) of said at least one surface-active agent (surfactant). At the same time, the covering layer of said at least one surfactant stabilizes the particles of the absorbing material, thereby preserving its sweat absorbency. Moreover, the covering layer constituted of the surface-active agent provides for homogeneous suspension of the absorber particles in the base formulation. Following application onto the skin, the water included in the base formulation evaporates/volatilizes, as a result of which the dehydrated product forms a thin film on the skin. Owing to this process, the surfactant can remain between the skin and the water-absorbing component. The surface-active agent supports the adherence of the water-absorbing component on the skin, mediating contact between the former and the skin, which contact allows absorption of sweat by the particles. Owing to the encapsulation, only a minor proportion of the water-absorbing component undergoes swelling in the water of the formulation, so that most of the water absorption capacity is available for sweat absorption. All in all, the high sweat absorption capacity of the absorber material is preserved for a longer period of time compared to well-known compositions.

The cosmetic product of the invention, especially the sweat-absorbing complex, has outstanding sweat absorption capacity, moisture reduction, inhibition of microorganisms and finally, substantial deodorizing benefit. The complex is suitable for incorporation in any cosmetic product, especially in hydrous products such as forearm deodorants.

According to particularly advantageous embodiments of the invention, the sweat-absorbing complex comprises
(a) 10 to 80%, particularly 20 to 70%, and preferably about 30 to 50% of at least one water-absorbing component,
(b) 10 to 70%, particularly 20 to 60%, and preferably about 30 to 45% of at least one surface-active agent,
(c) 0.05 to 15%, particularly 0.1 to 10%, and preferably about 1 to 5% of at least one electrolyte, and
(d) optionally 0 to 50% of at least one solvent and/or at least one vehicle.

The above ranges may vary strongly, depending on the properties of the individual components and the type of cosmetic product.

As a result of physical forces, such as hydrogen bridges and/or hydrophobic interactions between the polymer chains, said at least one electrolyte is preferably incorporated at least partially in the interstices of the polymer network of said at least one water-absorbing component. This conformation prevents excessively strong hydrogen bridges of the backbone chains of the water-absorbing component so that water/sweat can easily penetrate and push the absorber molecules apart to effect rapid hydration thereof. In other words, the inter- and intramolecular hydrogen bridges are cleaved by the electrolyte so as to facilitate the entry of water. Incorporation of electrolytes in the absorber material was shown to further increase the sweat or water absorption capacity of the polymer network and retain the water in the interstices. In this way, the electrolytes enhance the desired dry feeling on the skin.

Said at least one water-absorbing component is essentially insoluble in said at least one solvent and/or vehicle but, on the other hand, is capable of swelling in water without being completely dissolved in the water included in a base formulation of a cosmetic product. It has a water absorption capacity of at least 20%, particularly at least 50%, based on its dry weight. The mean particle size of the water-absorbing component in the complex ranges from 0.1 to 450 μm, particularly from 10 to 200 μm. Particles with a mean particle size between 50 and 100 μm show particularly good results.

The cosmetic product containing the sweat-absorbing complex described above can be selected from a diverse group of products. This group of products comprises deodorants (especially forearm deodorants), any deodorizing preparations, sticks, sprays, aerosols, creams, sunscreens, aftershaves, lotions, foundation creams, and make-ups. One advantage of the complex according to the invention is that it can be added easily to any standard preparations (base formulations), especially to hydrous formulations such as deodorant bases, without losing its water storage capacity. Typically, such products include 1 to 40 wt.-% water, particularly 3 to 20 wt.-%. Standard deodorant products are single-phase formulations and include about 12 wt.-% water.

Basically, the sweat-absorbing complex can be used in cosmetic products in a wide concentration range of from 0.05 to 99 wt.-%. Typically, the complex is included in a base formulation in a range of from 0.1 to 10 wt.-%, preferably from 0.25 to 5 wt.-%. In a deodorant base formulation the complex advantageously has a weight percentage between 0.1 and 10%, particularly about 1%. The actual deodorant base formulation usually includes 60 to 90 wt.-%, particularly 70 to 80 wt.-% of at least one solvent, 5 to 20%, particularly 10 to 15% water, and 1 to 15%, particularly 5 to 8% of at least one gelling agent.

It will be appreciated that the cosmetic product can include further auxiliary substances and/or active agents, e.g. pigments, colorants, antioxidants, preservatives, other moisture-retaining substances, softeners, fragrances (aromatic essences), stabilizers, cell turn-over promoters, cell proliferation stimulators, anti-inflammatory agents, antimicrobial agents, hormone regulators, enzyme inhibitors, UV absorbers, sunscreens and the like, and mixtures thereof.

As mentioned above, the cosmetic product according to the invention is remarkable for a coating/cover of the absorber particles of the sweat-absorbing complex by said at least one surfactant. This structure of the sweat-absorbing complex can be obtained by means of a method comprising the steps of
(a) mixing said at least one water-absorbing component with said at least one electrolyte,
(b) adding said at least one surface-active agent with stirring and heat supply until a homogeneous mixture is obtained, and, in case of using a solvent and/or vehicle,
(c) adding said at least one solvent and/or said at least one vehicle to the mixture of step (b) and mixing to form a substantially homogeneous mixture.

The application of thermal energy (heat) and shear forces (by stirring) in step (b) is crucial in causing rupture of inter- and intramolecular bonds within the surface-active agent and water-absorbing component and allowing generation of new physical interactions (especially hydrophobic interactions and hydrogen bridges) between said at least one surfactant and said at least one water-absorbing component in the subsequent cooling process. With no application of thermal energy and shear forces, surfactant(s) and water-absorbing component(s) merely develop very sparse physical interactions, and—following addition to a cosmetic base formulation—are unable to provide a cosmetic product with significant water absorption capacity.

To produce the cosmetic product, the thus prefabricated sweat-absorbing complex, already including the covered absorber particles, is simply added to a suitable base formulation, particularly to a hydrous deodorant base formulation.

Suitable substances for the particular ingredients of the sweat-absorbing complex will be referred to below.

Water-Absorbing Component

Said at least one water-absorbing component is selected from any natural or synthetic polymers capable of swelling in water to form a three-dimensional gel-like network.

The water-absorbing components most preferred herein are gums or gum-like polymers. In the context of the present invention, "gum" is generally defined as any watersoluble polymer isolated from terrestrial or marine plants or microorganisms, which is capable of contributing to viscosity and/or swellability of a dispersion thereof. The water-absorbing component is preferably a gum derived from vegetable or microbial biosynthesis of terrestrial or marine organisms. Such gums essentially include repeats of monosaccharide units and have relatively high molecular weights of preferably at least 100,000 g/mol. Examples of preferred gums are guar gums (*Cyamopsis tetragonolobus* gum), guar derivatives, locust bean gum, cellulose gum, gum arabic, gum karaya, tragacanth, gums derived from algae (comprising agar, carrageenan, furcellaran, and alginates), scleroglucan (sclerotium gum), tamarind seed gum, xanthan gum, dextran gum, gellan gum, propylene glycol alginate and the like, as well as derivatives and mixtures thereof.

Another preferred class of water-absorbing components are polysaccharides of vegetable origin, essentially comprising repeats of monosaccharide units of hexoses and/or pentoses. Specific examples comprise natural celluloses, natural fibers, cellulose derivatives, microcrystalline cellulose, carboxymethylcelluloses, methylcelluloses, hydroxyethylcelluloses, hydroxypropylcelluloses, hydroxypropylmethylcelluloses, pectins, maltodextrins, inulin, inulin derivatives, starch, starch derivatives, derivatives and mixtures thereof.

Another group of suitable water-absorbing components is selected from chemically modified polysaccharides, particularly from the group including cellulose derivatives, starch derivatives, pectin derivatives, starch/acrylamide/sodium acrylate graft copolymers (starch graft polymers), and mixtures thereof.

According to another embodiment of the invention, said at least one water-absorbing component is selected from polyacrylate-based synthetic polymers, essentially comprising repeats of acrylic acid, acrylamide, methacrylic acid, derivatives or mixtures thereof. Examples of such compounds comprise sodium polyacrylate, polyacrylamide, their copolymers and/or mixtures thereof.

Another group of preferred water-absorbing components is selected from silicic acids ($Si(OH)_4$ or $SiO_2$) and any types of derivatives and modifications thereof. Suitable examples comprise condensation products thereof, i.e., polysilicic acids (($SiO_2)_m \times nH_2O$), silicic anhydride (silica, $SiO_2$), fumed silica, hydrated silica ($SiO_2 \times H_2O$), silica gel, silicate esters and/or silicate salts such as sodium silicate, magnesium silicate and calcium silicate. It was found that the water absorption rate and capacity of these silica components can be dramatically enhanced by pre-dispersing them in an oil phase prior to the production of the complex.

Obviously, it is also possible to use mixtures of the abovementioned water-absorbing components.

Surface-Active Agents

As set forth above, said at least one surface-active agent assumes the function of forming a coating on the exterior surface of the particles of the water-absorbing component(s), thereby influencing the surface properties thereof. More specifically, the surface-active agents aid in retaining the polymer on the skin, protecting it from undesirable water absorption from the base formulation. Surface-active agents comprise compounds, including monomers, dimers, trimers, oligomers and polymers, which have lipophilic as well as hydrophilic functionalities of a strength sufficient to develop affinity to both hydrophilic and lipophilic portions of the formulation. Such agents form oriented layers around the water-absorbing particles. In this way, the particles of the water-absorbing component(s) are stabilized and distributed homogeneously within the formulation.

For the purposes mentioned above, the surface-active agent has a so-called hydrophilic/lipophilic balance (HLB) of below 13, particularly in the range of from 2 to 13, preferably from 3 to 11. Very good results are obtained with surfactants having an HLB ranging from 3 to 9, preferably from 4 to 8. The HLB is a dimensionless value developed by C. Griffin, which accounts for the relative amounts of lipophilic versus hydrophilic segments of a material. The assignment of numerical values for the HLB is based on effects of chemical groups within a molecule (D. L. Courtney, in "Surfactants in Cosmetics", $2^{nd}$ edition, Marcel Dekker, Inc., New York, 1997, 128-130).

According to a preferred embodiment of the invention, a mixture of at least two surface-active agents is used in the complex. In this event, it is also possible to use surfactants with HLB values outside the above-mentioned ranges, provided an effective weighted average HLB of such a combination falls within the above-mentioned ranges.

Said at least one surface-active agent can be a non-ionic, anionic, cationic or amphoteric compound or a combination thereof. Assorted examples include fatty alcohols, ethoxylated alcohols, ethoxylated triglycerides, ethoxylated oils, monoglycerides, carboxylic esters of alkyl or alkenyl glycols, $C_1$-$C_{40}$ fatty acid esters of polyols, $C_1$-$C_{40}$ fatty acid ethers of polyols, $C_1$-$C_{40}$ fatty acid esters of alkyl or alkenyl glycols, polyglycerol esters, polyglycerol esters of $C_1$-$C_{40}$ fatty acids, hydrocarbon-derived esters, sugar esters and polyesters, alkoxylated sugar esters and polyesters, ethoxylated carboxylic esters of $C_1$-$C_{40}$ fatty acids, sorbitan or polysorbate esters of fatty acids, ethoxylated sorbitan esters of fatty acids, ethoxylated sugar ethers of fatty acids, alkoxylated derivatives of $C_1$-$C_{40}$ fatty acid esters of $C_1$-$C_{40}$ fatty alcohols, alkoxylated derivatives of $C_1$-$C_{40}$ fatty acid ethers of $C_1$-$C_{40}$ fatty alcohols, polyethylene glycol ethers, polyethylene glycol esters, ethoxylated polysiloxanes, alkyl glycosides, alkanolamides, amine oxides, cetyl phosphate, potassium cetyl phosphate, diethanolamine cetyl phosphate, carboxylic acids and derivatives thereof, sulfonic acid derivatives, sulfuric acid derivatives, phosphoric acid derivatives, ethoxylated fatty ether phosphates, fatty acid amides, acyl lactylates, alkylamidoalkylamines, alkylamines, alkylimidazolines, alkyl-substituted amino acids, and mixtures thereof. Specific examples are saccharose stearate and sorbitan sesquioleate and mixtures of thereof.

Electrolytes

Said at least one electrolyte assumes the function of stabilizing the complex (especially the particles) and increasing the water absorption—by electrostatic repulsion interactions between the ions, forces between the polymer chains—and the osmotic pressure of the particles. In this way, the electrolytes retain the water within the particles and aid in maintaining the stability and structure of the particles.

Suitable electrolytes can be of one or more types selected from the group including alkali metal salts, ammonia, low-molecular weight amines, salts of di- or trivalent cations, phosphate salts, rock extracts, and mixtures thereof. Specific examples are sodium citrate, sodium chloride, potassium citrate, sodium hexametaphosphate, calcium chloride, calcium carbonate, and mixtures thereof.

The required weight percentages of the electrolyte in the water-absorbing complex depend on the physical and chemical properties of the electrolyte and of the other components.

Solvent/Vehicle

Optionally, a solvent and/or a vehicle is present in the sweat-absorbing complex. In general, this is required only in those cases where said at least one surface-active agent is a solid. In the event of a surface-active agent present in the form of a liquid, neither solvent nor vehicle are required.

Said at least one solvent and/or said at least one vehicle can be selected from the group including glycols, glycerol, polar and non-polar oils, hydrocarbons, ethers, esters, medium- and long-chain alcohols, alkoxylated alcohols, polyhydric alcohols, polyols, and mixtures thereof. Specific examples comprise propylene glycol, dipropylene glycol, ethylene glycol, glycerol, diglycerol, diacetin, triacetin, isopropyl palmitate, isododecane, isohexadecane, triglycerides, mineral oil, and mixtures thereof.

Further preferred embodiments of the invention can be inferred from other features specified in the dependent claims.

The invention will now be explained in more detail in the examples with reference to the pertaining drawings wherein.

(1) Production of the Sweat-Absorbing Complex

At least one water-absorbing component is placed in a clean, dry stainless steel tank equipped with a stirrer. Thereafter, at least one electrolyte is added. With slow stirring, the mixture is heated to a temperature between 50 and 100° C. and kept at this temperature. Subsequently, at least one surface-active agent is slowly added to the tank. While maintaining the batch temperature at 50-100° C., the mixture is stirred continuously for at least another 15 minutes, until a substantially uniform (homogeneous) mixture is obtained which does not include any undissolved raw materials. Depending on the particular ingredients, the complex thus produced has the consistency of a paste, soft solid or hard wax.

The precise quantities of the ingredients depend on the substances being selected.

Typical weight-based ratios are: water-absorbing component(s): electrolyte(s): surface-active agent(s) 50:5:45. The weight ratio of water-absorbing component(s) to surface-active agent(s) is 1: (0.25-2), preferably 1: (0.5-1.5). The preferred batch temperature for the process depends on the melting points of the ingredients, particularly those of the water-absorbing component and surface-active agent, and it varies between 50 and 100° C., particularly between 60 and 90° C. For most ingredients, a batch temperature between 70 and 80° C. is suitable.

When using a solid surface-active agent, a solvent and/or a vehicle is subsequently added to the mixture of water-absorbing component, electrolyte and surface-active agent, and stirring is continued until a homogeneous mixture with no undissolved raw material is present.

(2) Production of a Deodorant Stick 0.1-10 g, particularly 1-2 g of a sweat-absorbing complex produced according to (1) is added to a molten deodorant base formulation with continuous stirring at a batch temperature of 60-90° C., particularly 70-80° C., so as to obtain a homogeneous mixture of 100 g in total. The deodorant base formulation normally includes 60-90%, particularly 65-80 wt.-% of at least one solvent (for example, propylene glycol); 5-30%, particularly 10-25% water, and 1-15%, particularly 5-13% of at least one gelling agent (for example, sodium stearate). The mixture is subsequently cooled to room temperature to obtain the shape of a stick.

(3) Water Absorption Behavior of Various Water-Absorbing Components (Unprocessed) Raw Materials A defined quantity of each raw material (unprocessed water-absorbing component) was placed in a humidity cabinet with a relative humidity of 95-99% and incubated therein for eight weeks. The percent water absorption of each sample was calculated by differential weighing of the sample prior to and after incubation in the humidity cabinet and dividing the weight difference by the sample weight prior to incubation.

Figure 1:
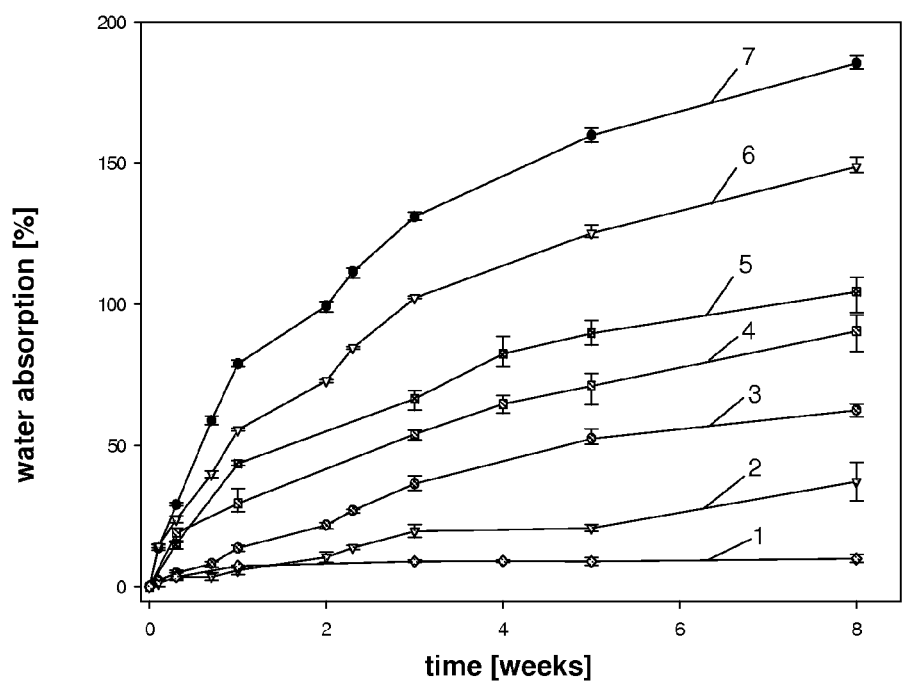
FIG. 1 shows the time profile of water absorption of various unprocessed water-absorbing components.

FIG. 1 shows the eight-week profile of water absorption of some examples of potential candidates for the water-absorbing component. Illustrated are the results of the following water-absorbing components: microcrystalline cellulose (curve 1), silicic anhydride (silica) (2), cellulose powder (3), polysaccharide gum (4), cellulose gum (5), starch graft polymer (6), and salt of a polyacrylic acid=sodium polyacrylate (7). The data clearly show that polysaccharide gum, cellulose gum, starch graft polymer and sodium polyacrylate (curves 4-7) each have a water storage capacity of more than 100%, based on the dry weight of the raw material. These components are therefore used with preference in the sweat-absorbing complexes according to the invention.

(4) Water Absorption Behavior of Various Water Absorbing Components in a Deodorant Base Formulation The unprocessed water-absorbing component (raw material; 5 g each time) was stirred with 95 g of molten deodorant base formulation (70-80 wt.-% propylene glycol, 10-15% $H_2O$, 5-8% sodium stearate) until to a homogeneous mixture was obtained. The mixture was cooled to room temperature to obtain the shape of a stick.

A defined quantity of each of these mixtures was placed on glass wool in a sealed container including an excess of water and subsequently incubated at 37° C. for 24 hours. A sample of pure deodorant base formulation was incubated in the container in the same way. After careful decanting of the excess water from the container, the percent water absorption was determined by differential weighing of each sample prior to and after water exposure.

Figure 2:
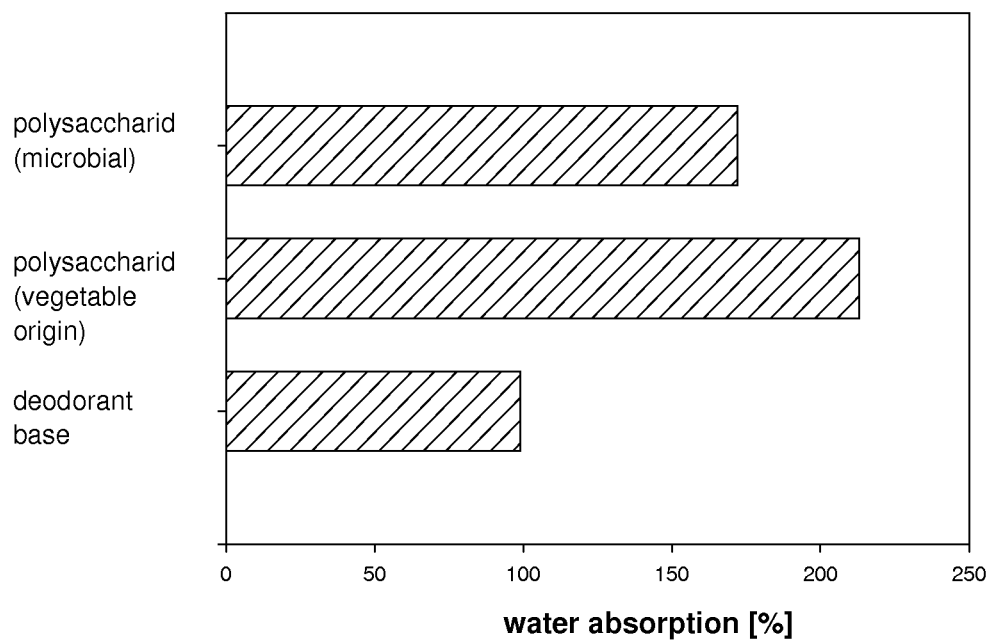
FIG. 2 illustrates the water storage capacity of unprocessed water-absorbing components in a deodorant base formulation.

The results for a polysaccharide gum from microbial biosynthesis (sclerotium gum from Alban Muller Ind.) and a polysaccharide gum of vegetable origin (blend of xanthan and *Cyamopsis tetragonolobus* gum (=guar) from TIC Gums, Inc.) are illustrated in FIG. 2. In addition, the water absorption of a pure deodorant base formulation is shown as reference. The results are given as grams of absorbed water per gram of deodorant base with or with no polysaccharide prior to incubation. The data show that the deodorants containing polysaccharide gums absorb 1.5 times the amount of water compared to a regular deodorant with no polysaccharide additive. It is thus demonstrated that addition of 1 wt.-% of polysaccharide gum provides an additional water storage capacity of 15 to 23% to a regular, hydrous deodorant base formulation.

(5) Water Absorption Behavior of Various Sweat-Absorbing Complexes in a Deodorant Base Formulation According to a First Embodiment of the Invention An electrolyte-containing sweat-absorbing complex in accordance with the present invention (complex A) and an electrolyte-free complex (complex B) were produced according to the procedure described above. The compositions of the two complexes are specified in Table 1.

1 g of each complex was stirred with 97.5 g of a molten deodorant base formulation (70-80 wt.-% propylene glycol, 10-15% $H_2O$, 5-8% sodium stearate) and 1.5 g of an aromatic essence until a homogeneous mixture was obtained. The mixture was cooled to room temperature to obtain the shape of a stick. Consequently, the products obtained included 1 wt.-% of the respective complex and 0.5 wt.-% water-absorbing component.

A defined quantity of each of these mixtures was placed on glass wool in a sealed container including an excess of water and subsequently incubated at 37° C. for 24 hours. After careful decanting of the excess water from the container, the percent water absorption was determined by differential weighing of each sample prior to and after water exposure.

Figure 3:
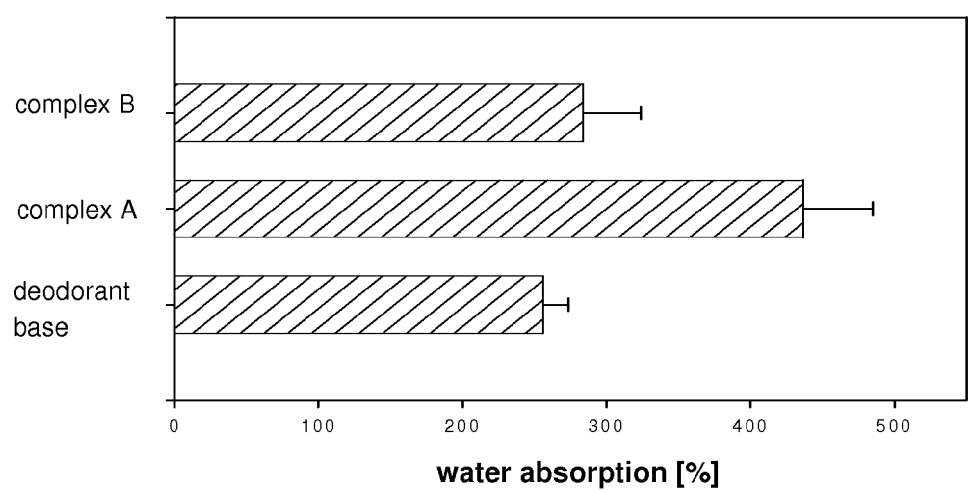
FIG. 3 illustrates the water storage capacity of sweat-absorbing complexes in a deodorant base formulation in accordance with a first embodiment of the invention.

The results for complexes A and B and for a pure deodorant base formulation including the aromatic essence are illustrated in FIG. 3. The increased water storage capacity of the pure deodorant base formulation, as compared to the deodorant base formulation in FIG. 2, is attributed to the aromatic essence which has a favorable influence on the water absorption. The data show that the deodorant with the complexes A and B can absorb more than 0.7 and 0.2 times, respectively, the amount of water compared to a regular deodorant. Moreover, the data demonstrate that the electrolytes have a very favorable influence on the water storage capacity of the absorber material. Ultimately, 1 wt.-% of polysaccharide gum added in the form of the complex according to the invention results in an additional water storage capacity of 360% compared to the regular deodorant base formulation. The example demonstrates that the sweat-absorbing complex of the invention results in a substantially higher water storage capacity compared to the pure water-absorbing component in the deodorant.

TABLE 1

| | Complex A | Complex B |
|---|---|---|
| Polysaccharide gum (xanthan + *Cyamopsis tetragonolobus* gum) | 50% | 50% |
| Surface-active agent, calculated HLB = 7.5 (saccharose stearate + sorbitan sesquioleate) | 45% | 50% |
| Electrolyte (sodium citrate) | 5% | — |
| Sum | 100% | 100% |

(6) Water Absorption Behavior of Various Sweat-Absorbing Complexes in a Deodorant Base Formulation According to a Second Embodiment of the Invention Two types of water-absorbing complexes (complexes C and D) with the compositions specified in Table 2 (in g or wt.-%) were produced in analogy to Example 5. Essentially, the complexes differ in the levels of electrolyte (sodium citrate). As described above, these complexes were incorporated in a deodorant base formulation to obtain deodorant products having the compositions specified in Table 3 (in g or wt.-%). The ranges specified in Tables 2 and 3 approximately represent the ranges covered in the test series, while the values in parentheses correspond to actual examples. Ultimately, the product containing complex C (Test 76-1) included 0.05 wt.-% electrolyte, and the product containing complex D (Test 76-2) included 0.001 wt.-% electrolyte. Similarly, a comparative example with no complex and thus no electrolyte was produced (Test 76-3).

The samples were weighed on glass wool in a sealed container. Following addition of water to the container, the samples were incubated at 37° C. for 24 hours. After careful decanting of the water, the samples were re-weighed, and the water absorption was determined by differential weighing prior to and after water exposure.

Figure 4:
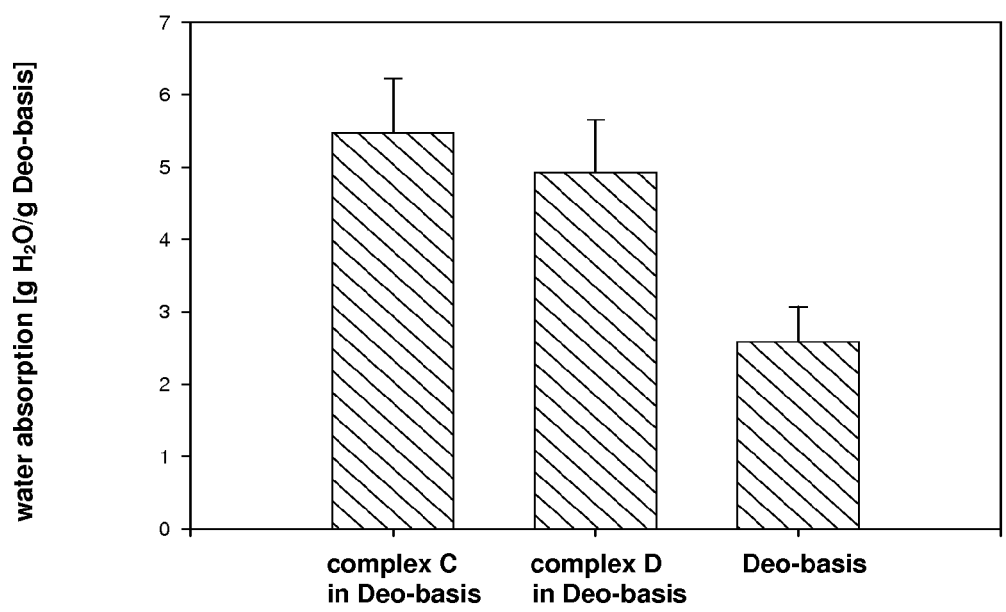
FIG. 4 illustrates the water storage capacity of sweat-absorbing complexes in a deodorant base formulation according to another embodiment of the invention.

Although the result illustrated in FIG. 4 shows a somewhat higher water absorption of the high-electrolyte sample, Test 76-1 (complex C), than the Test 76-2 (complex D) sample containing less electrolyte, this difference is less significant (according to the "Student T test" $p=0.28$ and $n=5$). On the other hand, the water absorption of the complex-containing samples Test 76-1 and 76-2 is significantly higher ($p<0.01$, $n=5$) than that of the complex-free sample Test 76-3 (pure deo base).

TABLE 2

|  | Complex C | Complex D |
|---|---|---|
| Propylene glycol | 30-35 (33.4) | 33-40 (36.6) |
| Sodium citrate | 3-5 (3.3) | 0.05-0.1 (0.07) |
| Natural cotton | 0.1-0.5 (0.2) | 0.1-0.5 (0.2) |
| Xanthan + guar gum | 30-35 (33.1) | 30-35 (33.1) |
| Saccharose stearate | 8-15 (10) | 8-15 (10) |
| Sorbitan sesquioleate | 18-23 (20) | 18-23 (20) |
| Sum | 100 | 100 |

TABLE 3

|  | Test 76-1 complex C in deo base | Test 76-2 complex D in deo base | Test 76-3 deo base |
|---|---|---|---|
| Propylene glycol | 65-70 (67.8) | 65-70 (67.8) | 67-72 (69.3) |
| Water, deionized | 17-23 (19) | 17-23 (19) | 17-23 (19) |
| Triclosan | 0.1-0.5 (0.3) | 0.1-05 (0.3) | 0.1-0.5 (0.3) |
| Sodium stearate | 7-12 (9) | 7-12 (9) | 7-12 (9) |
| Stearic acid | 0.5-1 (0.75) | 0.5-1 (0.75) | 0.5-1 (0.75) |
| Water abs. complex C (Tab. 2) | 1-2 (1.5) | — | — |
| Water abs. complex D (Tab. 2) | — | 1-2 (1.5) | — |
| Aromatic essence | a.r. | a.r. | a.r. |
| Allantoin | 0.1-1 (0.1) | 0.1-1 (0.1) | 0.1-1 (0.1) |
| Sum | 100 | 100 | 100 | a.r. = as required, depending on aromatic essence

The invention claimed is:

1. A sweat-absorbing cosmetic product, said product comprising
    i) a base formulation, and
    ii) a sweat-absorbing complex comprising
        (a) 0.1 to 90% of at least one water-absorbing component,
        (b) 0.1 to 80% of at least one surface-active agent,
        (c) 0.001 to 20% of at least one electrolyte, and
        (d) 0 to 50% of at least one solvent and/or at least one vehicle, wherein the sweat-absorbing complex is in the form of a three-dimensional polymer network of said at least one water-absorbing component, capable of swelling in contact with water, encapsulated by a coating of said at least one surface-active agent such that the at least one water-absorbing component is protected from absorption of water from the base formulation and further wherein the sweat-absorbing complex is emulsified in the base formulation, wherein the sweat-absorbing complex is obtained by premixing the at least one water-absorbing component, the at least one surface-active agent, the at least one electrolyte, and, optionally, the at least one solvent and/or at least one vehicle, with stirring, until a substantially uniform or homogeneous mixture is obtained, and further wherein the premixed sweat-absorbing complex is subsequently mixed with the base formulation to produce the sweat-absorbing cosmetic product.

2. The cosmetic product according to claim 1, wherein the at least one electrolyte has a weight percentage in the sweat-absorbing complex of 0.01 to 20 wt.-%.

3. The cosmetic product according to claim 1, wherein the sweat-absorbing complex comprises
    (a) 10 to 80 wt.-% of said at least one water-absorbing component,
    (b) 10 to 70 wt.-% of said at least one surface-active agent,
    (c) 0.05 to 15 wt.-% of said at least one electrolyte, and
    (d) 0 to 50 wt.-% of said at least one solvent and/or said at least one vehicle.

4. The cosmetic product according to claim 1, wherein at least part of said at least one electrolyte is incorporated in the interstices of the polymer network of said at least one water-absorbing component.

5. The cosmetic product according to claim 1, wherein the at least one water-absorbing component forms particles of a three-dimensional polymeric network when in contact with water.

6. The cosmetic product according to claim 5, wherein the at least one water-absorbing component forms particles with a mean particle size ranging from 0.1 to 450 μm.

7. The cosmetic product according to claim 1, wherein the at least one water-absorbing component has a water absorption capacity of at least 20% based on the dry weight thereof.

8. The cosmetic product according to claim 1, wherein the at least one water-absorbing component is essentially insoluble in said at least one solvent and/or vehicle.

9. The cosmetic product according to claim 1, wherein the at least one water-absorbing component is selected from gums from vegetable or microbial biosynthesis.

10. The cosmetic product according to claim 1, wherein the at least one water-absorbing component is selected from polysaccharides of vegetable origin.

11. The cosmetic product according to claim 1, wherein the at least one water-absorbing component is selected from chemically modified polysaccharides.

12. The cosmetic product according to claim 1, wherein the at least one water-absorbing component is selected from polyacrylate-based synthetic polymers.

13. The cosmetic product according to claim 1, wherein the at least one water-absorbing component is selected from silicic acids and derivatives and modifications Thereof.

14. The cosmetic product according to claim 1, wherein the at least one surface-active agent has a hydrophilic/lipophilic balance (HLB) ranging from 2 to 13.

15. The cosmetic product according to claim 1, wherein the complex has a mixture of surface-active agents having an effective weighted average hydrophilic/lipophilic balance (HLB) ranging from 2 to 13.

16. The cosmetic product according to claim 1, wherein the at least one surface-active agent is a non-ionic, anionic, cationic or amphoteric compound or a mixture thereof.

17. The cosmetic product according to claim 1, wherein the at least one electrolyte is selected from the group consisting of alkali metal salts, ammonia, low-molecular weight amines, salts of di- or trivalent cations, phosphate salts, stone extracts, and mixtures thereof.

18. The cosmetic product according to claim 1, wherein the at least one solvent and/or said at least one vehicle is selected from the group consisting of polar and non-polar oils, hydrocarbons, ethers, esters, medium-and long-chain alcohols, alkoxylated alcohols, polyhydric alcohols, polyols, and mixtures thereof.

19. The cosmetic product according to claim 1, wherein the product is selected from the group consisting of deodorizing preparations, sprays, aerosols, creams, sunscreens, after-shaves, lotions, foundation creams, and make-ups.

20. The cosmetic product according to claim 1, wherein the product has a water content of from 3 to 40 wt.-%.

21. The cosmetic product according to claim 1, wherein the sweat-absorbing complex has a weight percentage in the product of from 0.05 to 99 wt.-%.

22. The cosmetic product according to claim 1, further comprising auxiliary substances and/or active agents selected from the group consisting of pigments, colorants, antioxidants, preservatives, moisture-retaining substances, softeners, fragrances, stabilizers, cell turn-over promoters, cell proliferation stimulators, anti-inflammatory agents, antimicrobial agents, hormone regulators, enzyme inhibitors, UV absorbers, sunscreens, and mixtures thereof.

23. The cosmetic product according to claim 1, wherein the product is a deodorant containing 0.1 to 10 wt.-% of said sweat-absorbing complex in a deodorant base formulation.

24. The cosmetic product according to claim 23, wherein the deodorant base formulation includes 60 to 90% of at least one solvent, 5 to 30% water, and 1 to 20% of at least one gelling agent.

25. A method for the production of a cosmetic product comprising
  i) a base formulation, and
  ii) a sweat-absorbing complex comprising
    (a) 0.1 to 90% of at least one water-absorbing component,
    (b) 0.1 to 80% of at least one surface-active agent,
    (c) 0.001 to 20% of at least one electrolyte, and
    (d) 0 to 50% of at least one solvent and/or at least one vehicle, wherein the sweat-absorbing complex is in the form of a three-dimensional polymer network of said at least one water-absorbing component, capable of swelling in contact with water, encapsulated by a coating of said at least one surface-active agent, such that the at least one water absorbing component is protected from absorption of water from the base formulation, the method comprising the steps of:
  1) producing a sweat-absorbing complex by
    (a) pre-mixing at least one water-absorbing component and at least one electrolyte, and
    (b) adding at least one surface-active agent with stirring and heat supply until a substantially uniform or homogeneous mixture is obtained; and
  2) mixing the sweat-absorbing complex with a base formulation.

26. The method according to claim 25, further comprising the substep of (c) adding at least one solvent and/or at least one vehicle to the mixture of substep (b) and stirring until a substantially uniform or homogeneous mixture is obtained.

27. The method according to claim 26, wherein the substeps (a), (b) and/or (c) are performed at a temperature between 50 and 100° C.

* * * * *